(12) United States Patent
Weber (10) Patent No.: US 9,326,775 B2
(45) Date of Patent: May 3, 2016

(54) MAGNETIC DEVICE TO CONTROL OBESITY AND RELATED METHOD OF USE

(71) Applicant: BOSTON SCIENTIFIC SCIMED, INC., Maple Grove, MN (US)

(72) Inventor: Jan Weber, Maastricht (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/884,379

(22) Filed: Oct. 15, 2015

(65) Prior Publication Data

US 2016/0030220 A1 Feb. 4, 2016

Related U.S. Application Data

(63) Continuation of application No. 14/733,479, filed on Jun. 8, 2015, now Pat. No. 9,198,667, which is a continuation of application No. 13/785,738, filed on Mar. 5, 2013, now Pat. No. 9,066,780.

(60) Provisional application No. 61/611,263, filed on Mar. 15, 2012.

(51) Int. Cl.
*A61M 29/00* (2006.01)
*A61B 17/12* (2006.01)

(52) U.S. Cl.
CPC ..... *A61B 17/12022* (2013.01); *A61B 17/12159* (2013.01)

(58) Field of Classification Search
CPC ... A61F 5/0003; A61F 5/0006; A61F 5/0013; A61F 5/003; A61F 2210/0085; A61F 2002/30583; A61F 2002/5015; A61F 2/945; A61B 2017/00876
USPC ................ 606/192, 139, 151, 191, 144–148; 623/23.64, 23.65, 23.67, 23.71; 600/37; 604/195
See application file for complete search history.

(56) References Cited

U.S. PATENT DOCUMENTS 6,656,194 B1* 12/2003 Gannoe ................. A61F 5/0003
604/96.01
2009/0171383 A1* 7/2009 Cole ....................... A61F 5/003
606/192

* cited by examiner

*Primary Examiner* — Todd E Manahan
*Assistant Examiner* — Erich Herbermann
(74) *Attorney, Agent, or Firm* — Fay Kaplun & Marcin, LLP (57) ABSTRACT

A system for obesity control includes a sheath and a plurality of medical devices. The sheath has a proximal end, a distal end, and a lumen extending therebetween. The medical devices are disposed within the lumen. Each medical device includes a shell defining a cavity, the shell being movable between a deformed state and an unstressed state; a magnet disposed within the cavity; and a filler material disposed within the cavity. The filler material conforms to a shape of the shell when the shell is in the unstressed state. The filler material changes state to maintain a shape of the shell in the deformed state.

18 Claims, 6 Drawing Sheets

MAGNETIC DEVICE TO CONTROL OBESITY AND RELATED METHOD OF USE

PRIORITY CLAIM

The present application is a Continuation of U.S. patent application Ser. No. 14/733,479 filed on Jun. 8, 2015; which is a Continuation of U.S. patent application Ser. No. 13/785,738 filed on Mar. 5,2013, now U.S. Pat. No. 9,066,780 which claims the priority to the U.S. Provisional Application Ser. No. 61/611,263 filed on Mar. 15, 2012. The entire disclosure of these patents/applications are expressly incorporated herein by reference.

FIELD OF THE INVENTION

Embodiments of this disclosure relate to medical devices and procedures. In particular, embodiments of the instant invention relate to medical devices and procedures for the treatment of obesity.

BACKGROUND OF THE INVENTION

Obesity is a medical condition in which excess body fat accumulates to the extent that it may have an adverse effect on health. Medical practitioners have explored various surgical and non-surgical procedures for obesity management. Current medical methods for obesity treatment include surgery, gastric banding, intragastric balloons, and other related procedures.

A well-explored surgical technique for obesity treatment includes gastric bypass, a procedure that creates a malabsorptive state in the patient by reducing the size of the stomach and bypassing a portion of the small intestine. Another surgical procedure, gastric bypass Roux-en-Y and staples, reduces the capacity of the stomach by creating a smaller stomach pouch. Although these procedures are effective, they posses some disadvantages, such as "dumping syndrome", where the stomach contents are literally "dumped" rapidly into the small intestine, which may lead to nausea, weakness, sweating, faintness, and diarrhea.

Next to surgical methods, a patient may choose less invasive methods to lose weight. Gastric banding, for example, employs a gastric band, placed around the top portion of the stomach to restrict the amount of food that the patient can consume at one time. Unlike surgical procedures discussed above, gastric banding may be performed using minimally invasive techniques, and it does not require cutting or removal of part of the digestive system.

Another example of a non-surgical, non-pharmaceutical aid in the treatment of obesity is the Intra Gastric Balloon (IGB) system. In this treatment procedure, a surgeon inserts an empty balloon into a patient's stomach and then inflates the balloon with either sterile saline or air. After inflation, the expanded balloon cannot pass into the bowel, so it remains within the stomach. The inflated balloon occupies a large portion stomach volume producing a feeling of fullness even when the patient eats a small amount of food.

The conventional procedures noted above show positive results, but each method can result in harmful side effects and complications. The Intra-gastric balloon for instance, may cause obstruction within the intestine. For example, the balloon may become situated at the pylorus or within the small intestine. Other major complications reported through minimally invasive techniques of obesity management include— productive burping, gastritis, or slippage of an implanted gastric band, leading to inefficient obesity management.

Thus, a device that provides better obesity management is desirable.

SUMMARY OF THE INVENTION

In accordance with one embodiment, there is provided a medical device that includes a shell alterable between a deformed and an unstressed state defining a cavity, a magnet disposed within the cavity, and a filler material carried within the cavity conforming to the interior shape of the shell in the unstressed state and holding its shape in the deformed state. In some embodiments, the filler material converts from the deformed state to the unstressed state at a temperature equal to or less than human body temperature. The shell of the medical device may be spherical in shape and made up of a flexible material. In addition, the shell may include an antibacterial coating on its surface. Further, the magnet of the medical device may be rod-shaped and may be made up of a permanent rare-earth magnet such as neodymium. The medical device may also involve a filler to configure between the unstressed and deformed states. Here, the filler may include a fluid. Moreover, the medical device can employ a catheter to deform the device in ellipse shape during deployment.

Further, according to the disclosure, there is provided a method for obesity control, the method including introducing one or more medical devices into the stomach. The medical device can include a shell configurable between a deformed and an unstressed state defining a cavity, a magnet disposed within the cavity, and a filler material carried within the cavity conforming to the interior shape of the shell in the unstressed state and holding its shape in the deformed state. The method may further include formation of medical devices cluster held by magnetic interaction, and continuous rearrangement of cluster resulting from abdominal muscle energy expenditure and magnetic interactions. Here, the medical device is present in its deformed state while introduction in the stomach and reverts to the unstressed state within the stomach.

Still further, in some embodiments, the present disclosure also provides a system for obesity control, the system including a sheath having a proximal end, a distal end, a lumen extending there between, and one or more medical devices disposed within the lumen. The medical device may include a shell configurable between a deformed and an unstressed state defining a cavity, a magnet disposed within the cavity, and a deformation mechanism co-located with the magnet in the cavity. In addition, the system provides medical device, configured in a deformed state while within the lumen and an unstressed state after exiting from the distal end of the sheath. Here, the deformation mechanism includes a filler and a catheter. Typically, the configuration of the shell is spherical when in the unstressed state and elliptical in the deformed state. In addition, the device may be flexible with a coated shell and rod-shaped magnet.

Additional objects and advantages of the invention will be set forth in part in the description that follows, and in part will be obvious from the description, or may be learned by practice of the invention. The objects and advantages that the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts.

Embodiments of the present disclosure relate to devices, systems, and methods for obesity control. To this end, the device may substantially reduce food intake by filling a fraction of the stomach cavity. The medical device can include a shell defining a cavity containing a filler within the cavity, and a magnet disposed within the cavity of the shell. In addition, the medical device may be configured to alternate between an unstressed state and a deformed state using known mechanisms. In one embodiment of the present disclosure, the cavity defined by the shell may be filled with filler such as water. The medical device may be deformed by applying an external force, and the water may be frozen such that the device retains its deformed state without the application of force. When this device reaches the desired location in the patient's body, the ice may melt due to body heat, resulting in reversion of the medical device to its non-deformed unstressed state.

In use, two or more medical devices when implanted inside the stomach may form a cluster of the medical devices due to the strong magnetic interaction of the magnets. The individual medical devices are sufficiently small to be implantable in a body cavity, yet after forming a cluster of multiple individual medical devices, the resulting cluster may be too large to exit the cavity. In addition, the cluster may be designed such that the cluster may not create a blockage between the stomach and the small intestine or at any other location within the gastrointestinal tract (e.g., the esophagus, etc.). The uninterrupted abdominal muscle movement may exert a continuous force on the medical device cluster, leading to the continuous rearrangement of the cluster. In the process of rearrangement, the cluster may attempt to restructure itself continuously to overcome the magnetic interaction. The complete process may tire and strain the abdominal muscles, which may slow down the food processing leading to an increase in energy being expended during the digestion process. The decrease in food intake, reduced food processing rate, and increased energy expenditure during the digestion process may, in turn, control obesity.

In the following sections, embodiments of the present disclosure will be described using an exemplary body cavity—the stomach cavity. It will be understood that this choice is merely exemplary and that the device may be utilized in any other suitable body cavity, such as the colon, duodenum, bladder, esophagus, or any other appropriate cavity. Further, the medical device may be employed in any other known surgical procedures without departing from the scope of the present disclosure.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

Exemplary Embodiments

Figure 1:
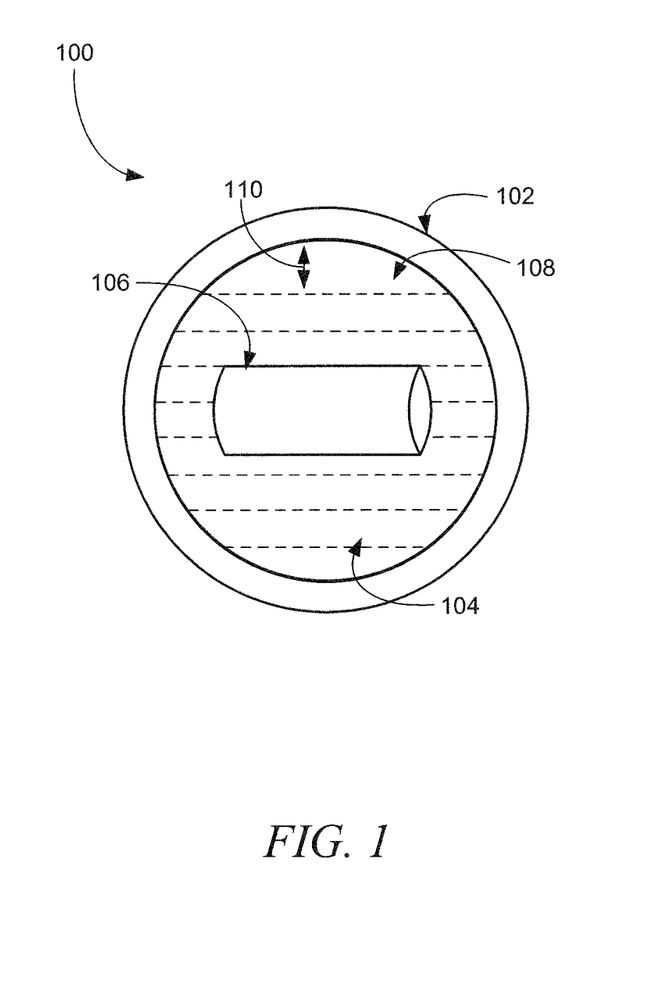
FIG. 1 illustrates an exemplary medical device according to embodiments of the present disclosure.

FIG. 1 illustrates an exemplary embodiment of a medical device 100 according to the present disclosure. The medical device 100 may include a shell 102, a filler 104, and a magnet 106. The shell 102 may define a cavity 108, which may house the magnet 106. A small amount of free space 110 (space occupied by air or any other compressible gas) may be left within the cavity 108.

The shell 102 may comprise flat spots on the edges or at the sides to better pack against the flat edges of another shell 102 when the shells 102 are clustered together. The shell 102 may take any of many three-dimensional shapes that may have flat surfaces, such as, for example, a pyramid, a diamond, or a cube. The shape of the shell 102 is not limited to shapes with flat surfaces, and a person skilled in the art may contemplate any other suitable shape for the shell 102. For example, in the illustrated embodiment, the shell 102 assumes a substantially spherical or spheroid shape. The shell 102 may assume any suitable dimensions appropriate for a desired application in a body cavity. For instance, when implanted within the stomach, the shell 102 may have dimensions greater than the size of pyloric sphincter to prevent obstruction of the duodenum. The shell 102 may have a thickness sufficient to hold the inner constituents and provide strength and stability to the medical device 100. In some embodiments, the thickness of the shell 102 may lie between about 2 mm and about 3 mm, but other dimensions may be appropriate for any specific use.

The shell 102 may be composed of any suitable material such as metals, alloys, natural or synthetic polymers, or any other material known in the art sufficient to maintain its integrity in the intended environment. Typically, the shell 102 may include a non-biodegradable, biocompatible material having sufficient flexibility to traverse body cavities and tracts. Additionally, as set out below, the shell material may be capable of elastic deformation, from the unstressed state to the deformed state, and back to the unstressed state. Such materials may include, but are not limited to, polytetrafluoroethylene (PTFE), fluorinated ethylene propylene, perfluoroalkoxy, polyvinylidene fluoride, silicone rubber, fluorinated polyurethane (PU), and other materials known to the art. Shell 102 may also include a range of materials, which can withstand the stomach pH ranging from about 1.5 to about 3.5.

Further, the shell 102 may have an antibiotic coating on its outer surface to inhibit growth of microorganisms on the surface. The coating (not shown) may contain an inorganic anti-biotic agent, disposed in a polymeric matrix that allows the antibiotic agent to adhere to the outer surface of the shell 102. The outer surface of the shell 102 may also have a coating of other materials such as drug-release, lubrication agents, or other coatings appropriate for the intended environment. Furthermore, the outer surface of the shell 102 may include coatings or agents configured to prevent erosion or digestion or to slow digestion of the shell 102 if degradability is desired. The coating may be provided over the shell 102 in any configuration and may coat one of a portion of the shell and the entire surface area thereof.

The magnet 106 may be a rod-shaped device having suitable dimensions based on the size of cavity 108. For example, the length of the rod-shaped magnet may vary from about 2 mm to about 20 mm, and the diameter may lie in range of 2 mm to 4 mm. It should be understood that other shapes for the magnet 106 might be contemplated, such as spheroid, rectangular, or trapezoidal. The shape of the magnet 106 may or may not have substantial effect on the functioning of the medical device 100. In addition, many small magnets may be used instead of a single magnet 106. Further, in some embodiments, the shell 102 may itself be magnetic and the separate magnet 106 may not be required.

Magnet 106 may be made of any suitable permanent magnet material having a magnetic field strength sufficient to hold two or more medical devices 100 in a cluster within the stomach. Such materials may include, but are not limited to, rare earth magnets including neodymium, samarium, alnico, and other suitable material known to the art. In one embodiment, the magnet may include a rod-shape neodymium magnet. Additionally, the magnet 106 may be shaped to accommodate desired shapes of the unstressed and deformed states of shell 102. In the illustrated embodiment, rod-shaped magnet 106 is employed, while others can call for a more compact cylindrical or button shape. Further, some embodiments may employ a collection of small magnets inside the medical device 100.

The filler 104 cooperates with shell 102 in morphing between deformed and unstressed states. In the unstressed state, the filler material does not retain a fixed shape, but rather conforms to the shape of its container. The filler material may be a fluid, a gel, or a flowable paste-like material. The filler material may condense or solidify in changing from the unstressed state to the deformed state (e.g., a physical state change from fluid to solid, as water freezes to form ice, or a change from glass to a semi-solid rubbery state in polymers creating a large difference in stiffness or viscosity of the polymer). This state change may allow convenient insertion of the medical device 100 within the body using minimally invasive techniques, as discussed below. The filler 104 may be water, air, oil, foam, or any other biocompatible substance that may change state and may assist in the deformation of the shell 102. In addition, filler 104 may be any fluid having desired physical and chemical characteristics appropriate for the intended environment. Some of the desired exemplary characteristics may include physical properties, such as, low density, and deformability while the chemical properties may include biocompatibility and low toxicity. One embodiment may employ water as an exemplary filler 104, but it should be clear that an embodiment might employ any appropriate filler material appropriate for the intended environment.

In some embodiments of the present disclosure, one or more of the shell 102, the filler 104 and the magnet 106 may be radiopaque or may be marked with a radiopaque material that may aid in imaging the medical device 100 with fluoroscopy. Further, other imaging modalities such as ultrasound may be used to image the medical device 100.

Figure 2:
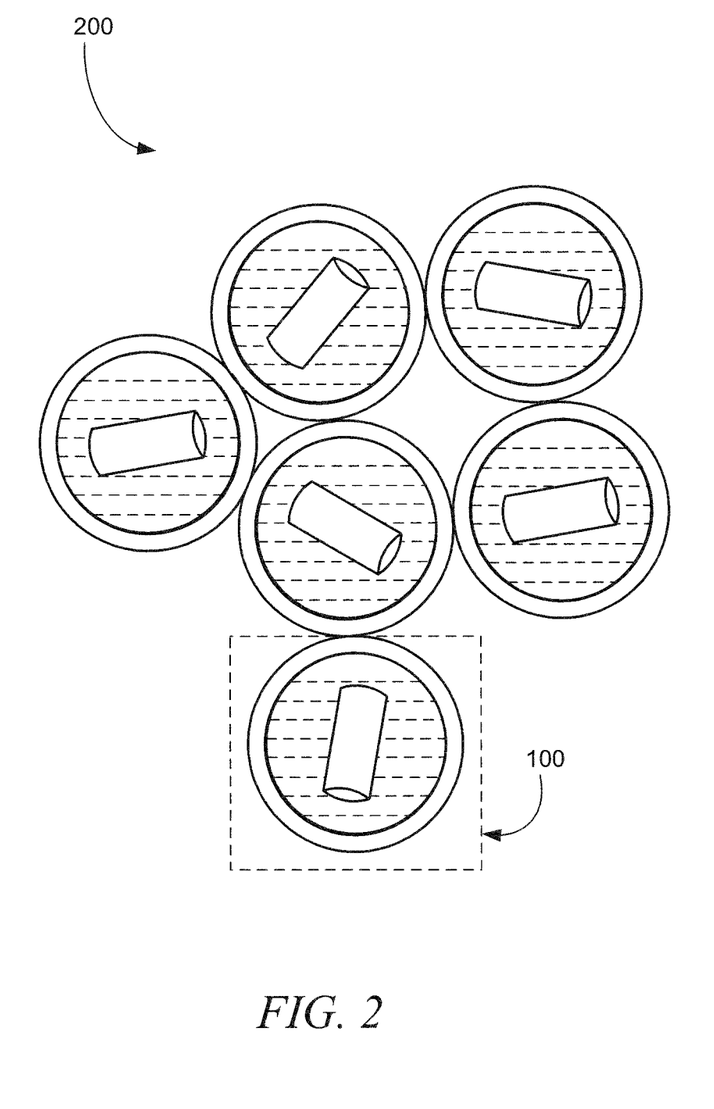
FIG. 2 is a schematic view of a cluster of medical devices according to one embodiment of the present disclosure.

FIG. 2 depicts a medical device cluster 200 of multiple medical devices 100. Magnets 106 cause adjacent medical devices 100 to clump, forming the medical device cluster 200. The shape of the medical device cluster 200 can be arranged by applying external force, so that movement of the stomach walls can rearrange the cluster. A surgeon can choose the number of medical devices 100 based on a desired volume of stomach capacity to be filled. Typically, the overall process of rearrangement consumes considerable abdominal muscle energy, which may slow down the food-processing rate, and amplify the effect of reducing food intake.

Figure 3:
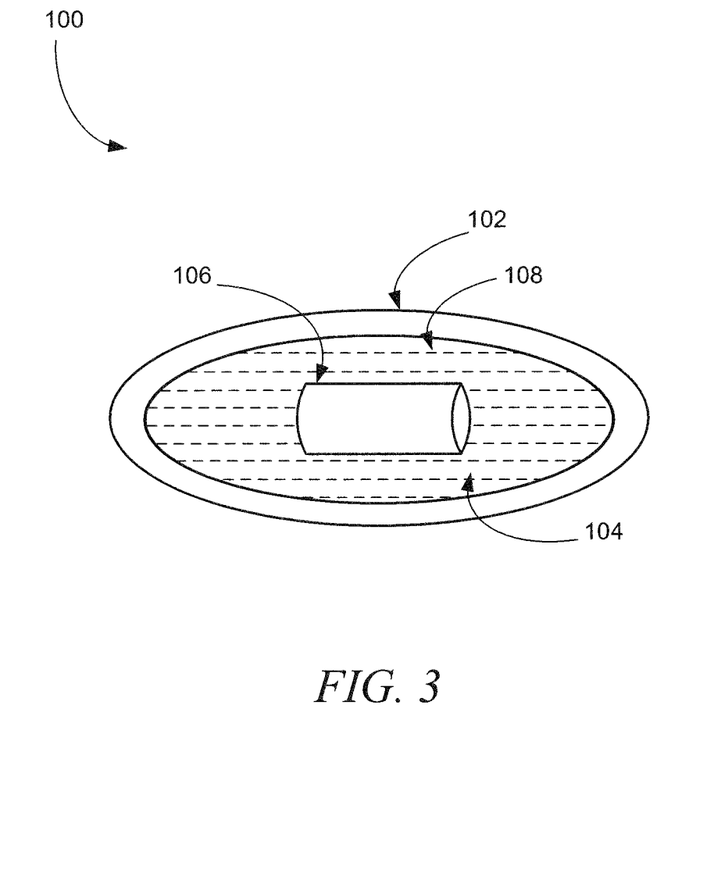
FIG. 3 illustrates the medical device (shown in FIG. 1) in a deformed state.

FIG. 3 illustrates the medical device 100 in a deformed state having, for example, a substantially elliptical shape. To achieve the deformed state may require separate actions to alter the state of the filler 104 and to alter the shape of shell 102. Those processes may proceed serially or in parallel. For example, the deformation process may include solidification of the filler (e.g., water) by freezing. In particular, the deformation process may include mechanical deformation of the medical device 100 to the desired deformed state followed by solidification of the filler to maintain the deformed state. The deformation of the shape of the shell 102 may involve pressing the flexible spherical shell 102 into an elliptical shape by applying a deforming force along one or more axial planes of the shell 102.

Subsequently, filler 104 (e.g. water) is solidified, which may involve alteration of the state change of the filler 104 by known mechanisms such as freezing. As can be seen in FIG. 1, freezing a water-based filler 104 may require leaving some free space 110 within the cavity 108, allowing for expansion of the water. The freezing mechanism may employ any method known in the art to reduce the temperature of the water 104 to its freezing point temperature (0 degree Celsius), such as refrigeration. The filler 104 retains the deformed shape of the shell 102 even after the removal of the deforming force. The elliptical shape of the deformed medical device 100 may be controlled by varying the strength of the deforming force applied on the shell 102 while freezing the water 104 within the shell 102. This deformed shape (elliptical) may be designed with a minor axis diameter that may be suitable for transport of the medical device 100 to the stomach cavity through the esophagus of a patient.

Figure 4:
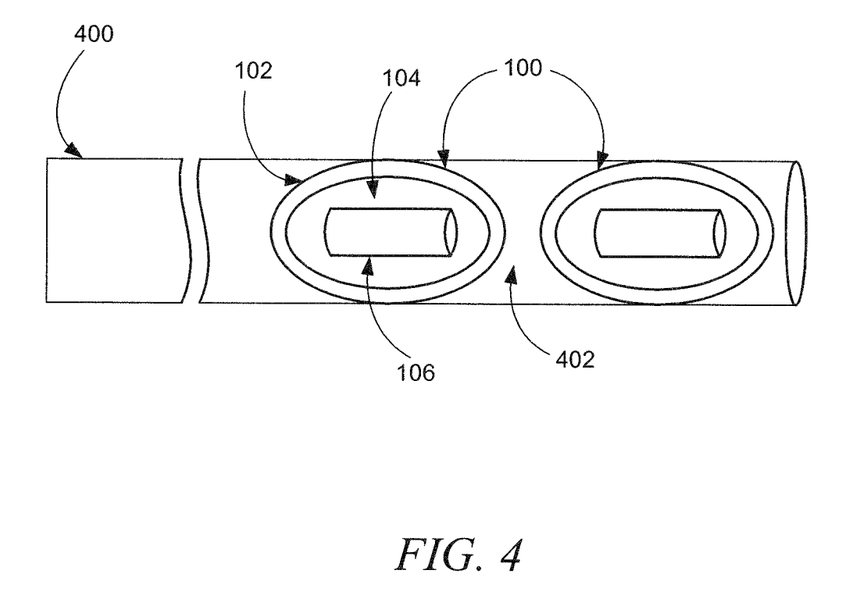
FIG. 4 illustrates a schematic-view of a deformed medical device of FIG. 3 enclosed inside a catheter lumen according to one embodiment of the present disclosure.

Implantation of the medical device 100 may involve an endoscope. The device may fit into a working channel of the endoscope and/or the device may be viewed using an endoscope on the side. In one exemplary embodiment, a hollow shell 102 about 2 cm in diameter (in an unstressed state), a wall thickness of 2 mm and an internal diameter of about 3 mm is deformed to an elliptical shape with a short axis diameter of about 7 mm. The device 100 may be inserted into the stomach via a catheter lumen 402 of about 7.5 mm internal diameter. To this end, it may be desirable that the short-axis diameter of the deformed medical device 100 should always be equal to or less than a diameter of the lumen 402. The lumen 402 may include a funnel shape at its proximal end to permit medical device 100 to be inserted in an unstressed or partially unstressed state. In some instances, the medical device 100 may be placed simply by following them.

FIG. 4 illustrates an insertion mechanism according to the invention. Here, the medical device 100 is introduced within a lumen 402 of a catheter 400. The catheter 400 may be any elongate member that may assist in inserting the medical device 100 within the body. Lumen 402 may exert a radially inward pressure on the medical device 100, keeping it in the deformed state. Once the member exits the lumen 402, however, the pressure is released, and the medical device 100 reverts to its unstressed spherical state (as shown in FIG. 1). In an embodiment, lumen 402 may include reinforcements, such as braids or coils, stronger lumen 402 material, or different lumen 402 wall thickness to strengthen the walls. In general, the stiffness of lumen 402 may exceed the stiffness of medical device 100 such that the medical device 100 remains in a deformed state within the catheter 400. The stiffness of the catheter 400 may be suitably chosen. If the lumen material is too thin or too elastic, it may not be sufficient to hold the medical device 100 in the deformed state and the medical device 100 may expand within the lumen itself. Alternatively, if lumen 402 is too rigid or thick, it may not be able to traverse the circuitous path within a patient's body. Therefore, it may often be preferred to select a suitable material and thickness of the lumen 402, keeping both aspects in mind.

In preferred embodiments, the medical devices 100 and the cluster 200 may have a weight and dimensions such that they may not be noticeable by the patient. The medical devices 100 may not weigh too much or move around too much during patient activity or eating. The medical device 100 may be designed to achieve well-compacted dimensions during deployment in a deformed state. The medical device 100 may be folded upon itself or may have geometric features that may aid in deformation such as corners or arms that may fold inwards.

Alternatively, the medical device 100 may be fabricated using shape memory material that allows transition of the medical device 100 from one shape to another upon exposure to a trigger, such as, body heat. In some embodiments, shape deformation of the shape memory material may be configured at a temperature higher that body temperature. Such configuration may require additional sources to increase the temperature of the medical device. For example, it may require the patient to consume a hot drink (for example, tea at 60° C.). Examples of shape memory materials may include, shape memory alloys such as Nitinol, shape memory polymers such as poly (c-caprolactone), poly (ethylene oxide), polybutadiene, poly (tetrahydrofuran), or any other suitable materials known to the art.

Other deformation mechanisms may include inflating the medical devices 100 within the stomach cavity through a valve disposed on the medical device 100 and an endoscopic filling mechanism. A person skilled in the art may contemplate any other feasible reversion mechanism appropriate for use in the environment of use without departing from the scope of the present disclosure.

In alternate embodiments, the medical device 100 may be utilized with other elements to perform additional functionalities. For example, the medical device 100 may house an electronic circuit, which may utilize the continuous changing configuration of the medical device cluster and thus the changing magnetic field to provide electric power to a circuit. The device 100 may utilize the change in electrical energy as an indicator of the rearrangement of the cluster, which may indicate the muscular movement of the stomach and thus the gastric activity of a patient. Further, the medical device 100 may house sensors to identify parameters associated with the stomach and the medical device 100. Suitable sensors such as pH sensors may be employed to identify acidity of the stomach, integrity of the shell 102, and so on.

Figure 5:
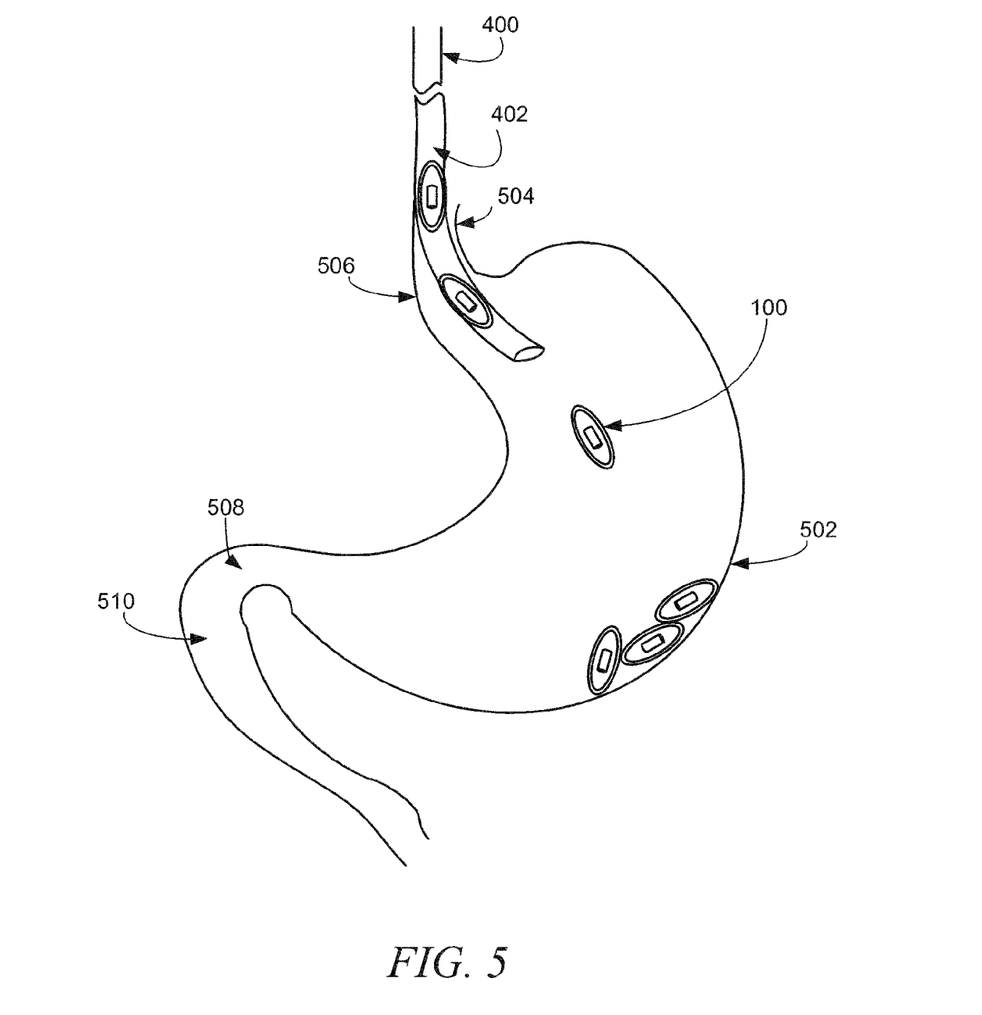
FIGS. 5 and 6 illustrate an exemplary method of using the medical device of FIG. 1 according an embodiment of the present disclosure.
Figure 6:
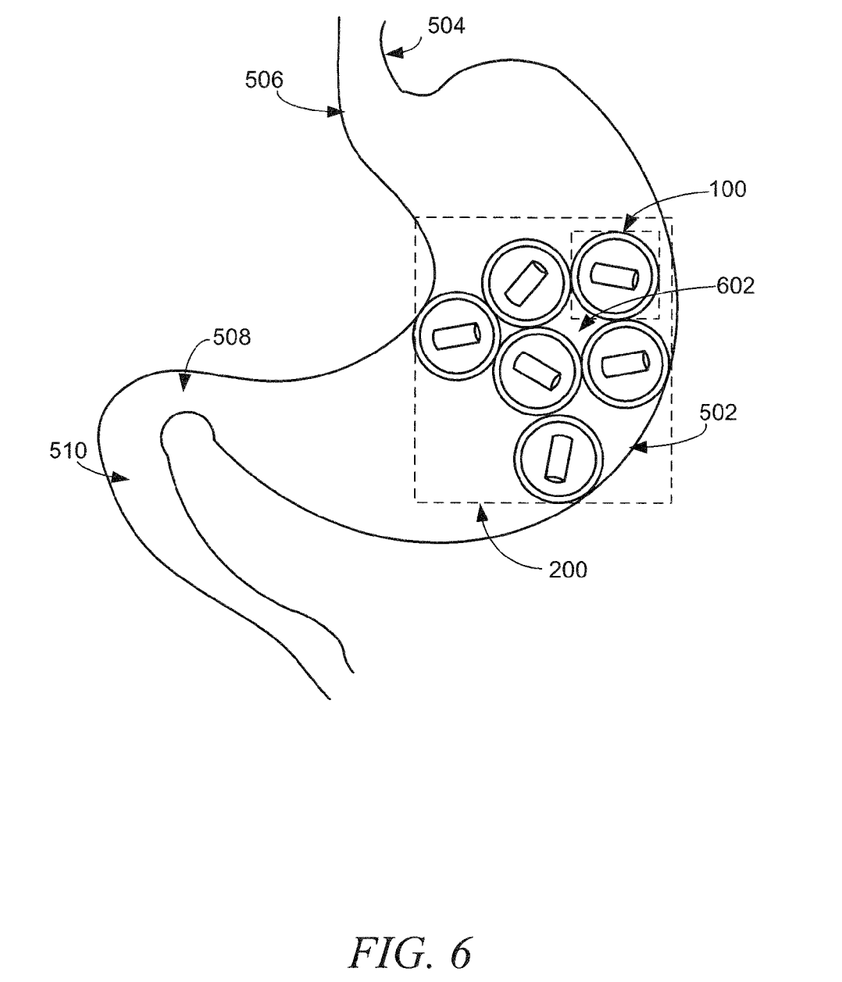

FIGS. 5 and 6 describe an exemplary method of using the medical device 100 for obesity control. As discussed previously, a physician may use the catheter 400 to deliver the deformed medical device 100 inside a patient stomach cavity 502. Catheter 400 may be a standard medical catheter or a customized medical catheter. The delivery of catheter may involve surgical incision, or may be passed through the mouth of the patient. Lumen 402 of catheter 400 is introduced inside patient's stomach, passing through esophagus 504 and lower esophageal sphincter 506. The physician may or may not give the patient a mild anesthetic to relieve the possible discomfort caused by catheter 400.

The physician may then introduce a predetermined number of the medical devices 100 inside the lumen 402. The deformation of medical device 100 may be done before or after loading the medical devices 100 inside the lumen 402. The delivery of deformed medical devices 100 into stomach cavity 502 includes forcing the deformed medical devices 100 distally. The force applied to the medical devices 100 may include a flushing fluid, compressed air, a mechanical means of the catheter, gravity, or any other suitable mechanism known to the art. After the delivery of the deformed medical devices into the stomach cavity 502, the physician may retract the catheter 400 leaving the deformed medical device 100 inside the stomach cavity 502 of patient for an extended period. The lumen 402 may have a diameter small enough to pass through the esophagus 504. The lumen 402 of the catheter 400 may have a diameter large enough to carry and transfer the deformed medical device 100.

Alternatively, the patient may ingest the medical devices 100 simply by swallowing. Each medical device 100 may be compressed in a biodegradable shell, such as gelatin or any polymer that may degrade quickly once the medical device 100 reaches the stomach.

Once positioned inside the stomach or other body cavity, the deformed medical devices 100 may revert to their unstressed shapes (e.g. spherical, as shown in FIG. 1). Elevated temperature or reduced pH of stomach cavity 502 may help in reversion of deformed medical device 100 to its unstressed shape. The unstressed medical device cluster 200 may occupy a sufficient space within the stomach cavity 502, which reduces the usable volume of the stomach cavity 502. This decrease in stomach cavity 502, usable volume may reduce the patient's food intake, which may provide for at least some effective obesity control.

Moreover, the medical device cluster 200 may exert an opposing force on the muscles of the stomach cavity 502. The uninterrupted muscular wall movement of stomach cavity 502 may exert continuous force on the medical device cluster 200, which may result in the continuous rearrangement of medical device cluster 200 to maintain equilibrium between the force exerted by the walls of the stomach and the magnetic force of attraction that exists between the medical devices 100. The rearrangement process of medical device cluster 200 may resemble the process of kneading dough. The energy consumed during this rearrangement process may strain the muscles of the stomach cavity 502, which may tire the stomach muscles involved in digestion, thus slowing the digestion process.

In one embodiment, the spherical configuration of medical device 100 may result in a medical device cluster 200 having a low device packing efficiency. Here, the low packing efficiency means that a number of voids 602 are created between the medical devices 100 due to the spherical shape of the medical devices 100 when closely packed together in the medical device cluster 200. In addition, during continuous rearrangement of the medical device cluster 200 food particles may be trapped inside the voids 602, with the size of the food particles trapped therein possibly reduced to smaller food particles, thereby possibly improving the digestion process. In any event, the medical devices 100 and the resulting cluster 200 are designed and intended so as not to create blockages to the normal digestion process.

In addition, the medical device cluster 200 may ensure safety of the patient from any intestinal blockages that may be caused by implanting the medical device 100 within the stomach cavity 502. The medical device 100 may be designed with an unstressed state dimensions that may prevent it from entering the duodenum 510 from the pyloric sphincter 508. The strongly magnetically bonded, medical device cluster 200 may further add to this safety measure by holding the medical devices 100 into a single clump and thereby preventing any medical device 100 from detaching from the medical device cluster 200 and move towards the pyloric sphincter 508. Further, the medical device 100 and the cluster 200 are designed to be non-noticeable by the patient, especially during physical activity or eating.

The medical device cluster 200 may be removed from the stomach cavity 502 using a retrieval process. Such process may include, but is not limited to, biopsy retrieval process, or any other suitable process known to the art. The biopsy retrieval process can squeeze each medical device 100, one by one, allowing each medical device 100 to be pulled back from the stomach cavity 502. In another exemplary embodiment, the magnetic property of the medical device 100 may be utilized to attract and hold each magnetic device 100 by a magnetic retrieval device. Retraction of the retrieval device results in removing the medical device 100 from the body. It is believed that there are numerous known other feasible retrieval mechanism that may be applied to retrieve the medical devices 100.

Alternatively, in some embodiments, the shell 102, and the filler 104 may be biodegradable and biocompatible. The medical device 100 may be designed to degrade over a certain period, such as a few weeks or a few months. The medical devices 100 may break down into components upon degradation and the magnets 106 may be designed to be small enough to pass through the patient's gastrointestinal tract naturally without causing gastrointestinal distress.

As discussed, the embodiments described herein facilitate efficient treatment of obesity. To this end, the embodiments employ a medical device cluster 200 to reduce the volume size of a patient's stomach cavity 502 and hence to limit the food intake into the stomach. In addition, the medical device cluster 200 operates in conjunction with the muscles of stomach cavity 502 to reduce the pace of food processing, increase muscular energy expenditure during digestion, and reduce the size of large food particles trapped inside the packing voids.

Other embodiments of the invention will be apparent to those skilled in the art from consideration of the specification and practice of the invention disclosed herein. It is intended that the specification examples be considered as exemplary only, with a true scope and spirit of the invention being indicated by the following claims.

What is claimed is:

1. A system for obesity control, comprising:
    a sheath having a proximal end, a distal end, and a lumen extending therebetween; and
    a plurality of medical devices disposed within the lumen, wherein each of the medical devices includes a shell defining a cavity, the shell being movable between a deformed state and an unstressed state; a magnet disposed within the cavity; and a filler material disposed within the cavity, the filler material conforming to a shape of the shell when the shell is in the unstressed state, the filler material changing state to maintain a shape of the shell in the deformed state.

2. The system of claim 1, wherein the medical device is insertable through the lumen into a stomach in the deformed state.

3. The system of claim 2, wherein the medical devices are permitted to revert to the unstressed state when released into the stomach.

4. The system of claim 1, wherein the magnets of the medical devices are selected to draw the medical devices together in a cluster within the stomach.

5. The system of claim 1, wherein the filler material is selected from the group comprising a fluid, a gel and a paste.

6. The system of claim 1, wherein the shell is substantially ellipsoidal when in the deformed state.

7. The system of claim 1, wherein the shells of the medical devices are flexible.

8. The system of claim 1, wherein the magnet in at least one of the medical devices is rod shaped.

9. The system of claim 1, wherein the shell includes at least one flat surface.

10. The system of claim 1, wherein at least one of the shell, the magnet and the filler material includes a radiopaque material.

11. The system of claim 1, wherein each medical device further includes an electronic circuit.

12. The system of claim 1, wherein each medical device further includes a sensor to identify parameters of one of a stomach in which the medical device is inserted and the medical device.

13. The system of claim 12, wherein the sensor is a pH sensor.

14. The system of claim 1, wherein the shell includes an antibiotic coating on an outer surface thereof.

15. The system of claim 1, wherein the shell includes a coating for one of controlling drug release, controlling digestion, preventing erosion and providing lubrication.

16. The system of claim 1, wherein the sheath includes a funnel-shape at the proximal end thereof.

17. The system of claim 1, wherein a stiffness of the sheath is greater than a stiffness of each of the medical devices.

18. The system of claim 1, wherein the shell is formed of a shape memory material.

\* \* \* \* \*